United States Patent [19]
Sidot

[11] Patent Number: 5,914,429
[45] Date of Patent: Jun. 22, 1999

[54] INDUSTRIAL PROCESS FOR THE CONTINUOUS PREPARATION OF SODIUM ORTHOHYDROXYMANDELATE

[75] Inventor: Christian Sidot, Compiegne, France

[73] Assignee: Clariant (France) S. A., Puteaux, France

[21] Appl. No.: 09/033,435

[22] Filed: Mar. 2, 1998

[30] Foreign Application Priority Data

Mar. 11, 1997 [FR] France .................................. 97 02847

[51] Int. Cl.⁶ .................................................. C07C 59/48
[52] U.S. Cl. ............................................................. 562/470
[58] Field of Search ............................................. 562/470

[56] References Cited

U.S. PATENT DOCUMENTS

| | | |
|---|---|---|
| 4,198,523 | 4/1980 | Copeland et al. . |
| 4,368,334 | 1/1983 | Dales . |
| 4,408,070 | 10/1983 | Schouteeten et al. . |
| 4,504,678 | 3/1985 | Schouteeten et al. . |
| 5,248,816 | 9/1993 | Schuttleworth . |

FOREIGN PATENT DOCUMENTS

| | | |
|---|---|---|
| 650172 | 4/1993 | Australia . |
| 0 556 084 | 8/1983 | European Pat. Off. . |
| 368696 | 5/1990 | European Pat. Off. . |
| 536960 | 4/1993 | European Pat. Off. . |
| 2 495 137 | 6/1982 | France . |

*Primary Examiner*—Paul J. Killos
*Attorney, Agent, or Firm*—Browdy and Neimark

[57] ABSTRACT

In an industrial process for the manufacture of sodium orthohydroxymandelate by condensation of phenol in an inert atmosphere with glyoxylic acid in aqueous solution, in the presence of a tertiary amine and of catalytic quantities of a trivalent metal cation at a temperature below 100° C., carried out continuously in at least two reactors (R1 . . . Rn) installed in series, the first being supplied by a first tank C1 containing the glyoxylic acid and the trivalent metal cations, and a second tank C2 containing the phenol and the tertiary amine, the reaction medium obtained at the outlet of the last of the at least two reactors and consisting of an aqueous phase and an organic phase is transferred into the first of two mixer-decanters (MD1 and MD2) installed in series, the aqueous phase of the first mixer-decanter MD1 is recovered in order to extract the expected sodium orthohydroxymandelate from it, while the organic phase that has come from MD1 is transferred into the second mixer-decanter MD2 and washed with water, and the organic phase of the second mixer-decanter MD2 is transferred to the second tank (C2).

21 Claims, No Drawings

INDUSTRIAL PROCESS FOR THE CONTINUOUS PREPARATION OF SODIUM ORTHOHYDROXYMANDELATE

The present invention relates to an industrial process for the continuous preparation of sodium orthohydroxymandelate, by hot condensation of glyoxylic acid with phenol in the presence of a tertiary amine and of catalytic quantities of trivalent metal cations.

Sodium orthohydroxymandelate can be used for the batch manufacture of orthohydroxymandelic acid as described in FR-A-2,687,143. It is a valuable intermediate for obtaining either the orthohydroxyphenylacetic acid used to obtain molecules having interesting plant-health properties, or for obtaining molecules of the ethylenediamine N,N'-bis(2-hydroxyphenylacetic) or EDDHA type capable of forming complexes, in particular with iron or manganese, or for obtaining new fungicides.

It is known that glyoxylic acid condenses with phenol in an alkaline aqueous medium to lead to a mixture of ortho- and parahydroxymandelic acids, as well as to -2,4 and -2,6-substituted hydroxybenzenediglycolic acids.

It is also known that, in an alkaline aqueous medium, glyoxylic acid is dismuted according to Cannizzaro into oxalic and glycolic acids. FR-A-2,440,350 describes how, by reacting glyoxylic acid with phenol for some minutes, at high temperature, in an alkaline aqueous medium, it was possible to minimize Cannizzaro's reaction and excite the condensation reaction and thus be able to achieve a 70 to 85% yield of parahydroxymandelic acid.

It is also known to prepare parahydroxymandelic acid with a good selectivity, in a quasi-anhydrous medium, in a non-continuous manner, by reacting glyoxylic acid with phenol, in the presence of an excess of suitable tertiary amine such as tributylamine (as described in FR-A-2,638,740).

A. J. Hoefnagel et al, Rec. Trav. Chem., 107, 242–7 (1988) showed that the condensation of glyoxylic acid with phenol could be catalysed by certain metal ions and that, operating in a dilute aqueous medium, at pH=5, at 100° C., in the presence of trivalent metal cations such as aluminium, chromium and iron, it was possible to obtain high selectivities in ortho position. However, because of a substantial dilution which delivers a low productivity on the one hand, and, on the other, the obtaining of a high level of disubstituted products which leads to complex mixtures from which it is then difficult to isolate the sought orthohydroxymandelic acid, this process is not industrially economic.

WO-A-94.14746 describes a method of separating ortho and para isomers of the alkaline salts of hydroxymandelic acid by selective extraction of the aqueous mixtures. By carrying out an extraction of the mixture with a polar aprotic organic solvent, for example acetone, methylketone, tetrahydrofuran, ethyl acetate, it was found that the ortho isomer sodium salt was very soluble in these solvents. But such a process requires numerous extractions and evaporations and the repeated used of solvents, which makes the process difficult to use industrially, costly and a source of pollution. Moreover, none of the obtained products has the required purity in certain applications such as for example the synthesis of active principles for the pharmaceutical or plant-protection industries.

FR-A-2,687,143 which was mentioned previously describes a batch preparation method allowing orthohydroxymandelic acid to be obtained with a yield that may be as much as 86.5% by condensation of glyoxylic acid on phenol in the presence of a tertiary amine, preferably tributylamine and catalytic quantities of trivalent metal cations, preferably $Al_2(SO_4)_3$, the secondary products of this reaction being parahydroxymandelic acid and a disubstituted product in a very small quantity. But there remained the isolation of the orthohydroxymandelic acid or its alkaline salts in the pure state.

To prepare sodium orthohydroxymandelate continuously in an industrial plant according to the general principle described in FR-A-2,687,143, it was necessary to determine, then control the essential parameters of this condensation, so as to reduce the secondary reactions mentioned previously in order to obtain the best possible yield from the glyoxylic acid used. It was also essential that this process permit a maximum recycling of all the raw materials that are used and not transformed. It is also necessary for the process to have a satisfactory hourly productivity in order to produce a profit on the investments made. A reliability of the plant was required and the process had to deliver a correct selectivity of condensation in order to minimize the quantities of secondary products and in particular sodium parahydroxymandelate. Finally, the process had to lead to the lowest possible operating costs.

The applicant attempted to realize the condensation of phenol with glyoxylic acid, by reaction in a series of reactors. But when operating in a concentrated medium a major problem of blockage occurred when transferring the reaction mixture between the first and second reactors.

After lengthy additional studies, this problem was resolved by reacting phenol with glyoxylic acid in aqueous solution in the presence of a tertiary amine and catalytic quantities of trivalent metal cations successively in at least two reactors, the resulting mixture being treated successively in two mixer-decanters, the solvent phase that has come from the second mixer-decanter being returned to the starting products.

This is why the subject of the present invention is an industrial process for the continuous manufacture of sodium orthohydroxymandelate by condensation of phenol in an inert atmosphere with glyoxylic acid in aqueous solution, in the presence of a tertiary amine and catalytic quantities of a trivalent metal cation at a temperature below 100° C., characterized by the fact that the process is carried out continuously in at least two reactors (R1 . . . Rn) installed in series, the first being fed by a first tank C1 containing the glyoxylic acid and the trivalent metal cations, and by a second tank C2 containing the phenol and the tertiary amine, the reaction medium obtained at the outlet of the last of the at least two reactors and consisting of an aqueous phase and an organic phase is transferred into the first of two mixer-decanters (MD1 and MD2) installed in series, the aqueous phase of the first decanter-mixer MD1 is recovered in order to extract the expected sodium orthohydroxymandelate from it, while the organic phase that has come from MD1 is transferred into the second mixer-decanter MD2 and washed with water, and the organic phase of the second mixer-decanter MD2 is transferred to the second tank (C2).

The starting glyoxylic acid is preferably used in aqueous solution, for example 40 to 60% by weight, and preferably about 50% (industrial-grade glyoxylic acid).

The starting phenol used is for example at a concentration of 75 to 95% by weight in water, in particular at a concentration of 85 to 95% by weight in water and preferably at a concentration of about 90% by weight in water.

The tertiary amines used can be soluble in water, such as dimethylaminopropanol, dimethylaminodiglycol, tetramethylene-diamine. Preference is given to tertiary amines which are insoluble in water, such as trihexylamine, N-tripropylamine, triisononylamine, dimethylcyclohexylamine and, for preference, tributylamine to recover them at the aqueous extraction phases stage.

Suitable trivalent metal cations include chromium III, iron III, aluminium III, gallium III, indium III, thallium III, ruthenium III and scandium III cations, but preferably chromium III, iron III and aluminium III cations, and quite particularly this latter.

A particularly advantageous pairing of tertiary amine and trivalent metal cation consists of tributylamine and aluminium.

Under preferred implementation conditions, the above process is characterized in that the organic phase that has come from the second mixer-decanter MD2 is mixed with an aqueous solution of phenol and concentrated in order to eliminate all or part of the aqueous phase, then sent to the second tank (C2).

In a preferred manner, the process is characterized by the fact that the residence time of the reaction medium in each of the reactors is between 30 and 120 minutes, in particular about 45 mm.

Under other preferred conditions, the aqueous phase coming from the first mixer-decanter (MD1) is sent into an extraction column (S) where it is mixed with an ether which dissolves phenol and the tertiary amine, the organic phase which results from this being sent to the second tank (C2) at the same time as that which has come from the second mixer-decanter (MD2), while the aqueous phase containing the expected sodium orthohydroxymandelate is recovered.

Under yet other preferred operating conditions, three reactors are used in series and the temperature of the first reactor is between 30 and 80° C., that of the second reactor between 70 and 90° C., and that of the third reactor between 70 and 90° C.

Under quite particularly preferred conditions, the process is carried out in three reactors kept at 75±5° C. for the first, 85±5° C. for the second and third reactors.

Under still other preferred conditions, the process of the invention is also characterized by the fact that the mixture which has come from the 3 reactors in series is sent into two successive mixer-decanters MD1 and MD2. This mixture is sent into MD1 at the same time as an aqueous soda solution, and the aqueous phase 1 of this first mixer-decanter MD1 is sent to a stirred extraction column, S, whence the final sodium ortho-hydroxymandelate solution will be extracted. The second mixer-decanter MD2 is used to wash the organic phase leaving MD1 with water before its return into the process to the second tank (C2).

The process of the invention is also characterized in particular by the fact that the organic phase leaving the extraction column S is sent to a concentrator D, preferably at the same time as the organic phase coming from MD2.

Under preferred operating conditions, the molar proportion of the starting reagents is:
1 to 15 moles of phenol,
0.8 to 1.2 moles of tertiary amine,
0.001 to 0.1 mole of trivalent metal cation for one mole of glyoxylic acid.

The starting reagents advantageously come from 2 feed tanks, one, C1, containing the glyoxylic acid and the trivalent metal cation, the other, C2, containing the tertiary amine and the phenol. These tanks preferably supply the first reactor continuously, at a constant rate of feed, with an aqueous solution containing, for 1 mole of glyoxylic acid, 1 to 15 moles of phenol, 0.8 to 1.2 moles of tertiary amine, and 0.001 to 0.1 mole of trivalent metal cation.

Under yet other preferred conditions for using the above process, the reaction mixture of R1 runs by overflowing into a reactor R2 then into a reactor R3.

At the outlet of the last reactor, for example R3 if there are three reactors, the reaction mixture is sent into a first mixer-decanter MD1 into which are added in particular an alkaline hydroxide, preferably sodium or potassium, and an ether which dissolves the phenol and the tertiary amine, such as methyl tert-butyl ether (MTBE), diisopropyl ether (DIPE) or preferably tert-amyl methyl ether (TAME). The soda is advantageously used jointly with the TAME. 2 distinct phases are obtained: an aqueous phase 1 and a solvent phase 1.

The solvent phase 1 passes, preferably by overflowing, into a second mixer-decanter MD2, where it is washed with water. The effect of this washing is to extract the remainder of the mandelates from the organic phase.

At the outlet of MD2, 2 phases are recovered anew: an aqueous phase 2 and a solvent phase 2. Aqueous phase 2 is sent to MD1 and serves in part to dilute the sodium hydroxide: solvent phase 2 is sent to tank C2 via a concentrator D.

With a view to isolating the sodium orthohydroxymandelate, the aqueous phase 1 is preferably sent to an extraction column S. The organic phase leaving the extraction column S is advantageously sent to a concentrator D at the same time as the solvent phase 2.

In the concentrator D, the water and the TAME are advantageously eliminated and will then be able to be recycled into the process.

In a still more preferred manner, the process is characterized by the fact that the starting aqueous solution contains, for 1 mole of glyoxylic acid, 12 moles of phenol, 1.05 moles of tributylamine, and 0.005 mole of aluminum sulphate. In other preferred conditions for using the invention, the reactors R1, R2 and R3 have a respective capacity of 5 m$^3$, 10 m$^3$ and 10 m$^3$. In yet other preferred conditions for using the invention, the contact times of the reagents in each of the reactors is about 45 mn. In wholly preferred conditions, the temperatures of the reactors R1, R2 and R3 are respectively 75, 85 and 85° C.

In a preferred embodiment, the reaction mixture which has come from the 3 reactors is sent to 2 mixer-decanters in series, MD1 and MD2, preferably with a capacity of 2 m$^3$. The aqueous phase 1 of the first mixer MD1 is advantageously sent to a stirred extraction column S, in particular of diameter DN 450 from which the desired sodium orthohydroxymandelate is recovered in aqueous solution.

EXAMPLE 1 a) Preparation of the reagents

In a 250-liter tank C1, a pre-mixing is carried out of glyoxylic acid in 50% by weight aqueous solution and aluminium sulphate in 37% aqueous solution in a molar ratio of $$\frac{\text{glyoxylic acid}}{Al^{3+}} = \frac{1}{0.05}$$

the whole being heated to 60° C.

In a tank C2, capacity 25 m$^3$, a tributylamine-phenol mixture is prepared in a molar ratio of $$\frac{\text{tributylamine}}{\text{phenol}} = \frac{1.05}{12}$$

The internal temperature of this tank C2 is controlled at 75° C., and it is connected to a concentrator D.

b) Reaction stage in the 3 reactors R1, R2 and R3

Starting from the mixtures contained in the tanks C1 and C2, a first reactor R1, capacity 5 m$^3$, is supplied at a rate of feed such that the glyoxylic acid/aluminum sulphate/tributyl-amine/phenol molar ratio is equal to 1/0.05/1.05/12 and the residence time in this reactor is 45 mn. The internal temperature of this reactor is 75° C.

The reaction mixture runs by overflowing into a reactor R2, capacity 10 m³, where it is kept at 85° C. for 45 mn, then into a reactor R3, capacity 10 m³, where it is kept at 85° C. for 45 mn.

c) Separation stages of the reaction products

At the outlet of this reactor R3 the reaction mixture, called MR, is sent to a mixer-decanter MD1, capacity 2 m³, which is kept at a temperature of 54° C.

There is continuous addition to MD1 of sodium hydroxide diluted to 17%, prepared from 47% sodium hydroxide and water part of which comes from the decantation of the azeotrope obtained in the decanter D and part of which comes from the mixer-decanter MD2, so as to observe a molar ratio of $$\frac{\text{sodium hydroxide}}{\text{glyoxylic acid}} = 1.8$$

Tert-amyl methyl ether (TAME) is also added to MD1 so as to observe a molar ratio of $$\frac{TAME}{\text{reaction medium}} = 0.5$$

At the outlet of MD1, 2 distinct phases are drawn off: an aqueous phase 1 and a solvent phase 1.

Solvent phase 1 passes by overflowing into a second mixer-decanter (MD2), capacity 2 m³, where it is washed with water, in such a way that the ratio by volume $$\frac{\text{water}}{\text{solvent phase 1}} = 0.2$$

At the outlet of MD2, 2 phases are recovered anew: an aqueous phase 2 and a solvent phase 2. Aqueous phase 2 is sent to MD1 and serves in part to dilute the sodium hydroxide, solvent phase 2 is sent to a concentrator D.

The aqueous phase 1 is sent to a stirred extraction column S, diameter DN 450, which allows the desired sodium ortho-hydroxymandelate to be recovered.

In this extraction column, the extraction is carried out at 35–40° C. of the phenol solubilized in aqueous phase by TAME $$\left(\text{ratio by volume } \frac{\text{aqueous phase 1}}{TAME} = 1.8\right)$$

The organic phase leaving this extraction column S is sent to the concentrator D at the same time as the solvent phase 2 and the 90% phenol at a rate of feed such that the molar ratios $$\frac{90\% \text{ phenol}}{\text{entering solvent phase phenol}} = \frac{1}{11}$$

In the concentrator D, the water and the TAME are eliminated, and will then be recycled into the process. After concentration a solution is obtained $$\frac{\text{tributylamine}}{\text{phenol}} \text{ in the molar ratio } \frac{TBA}{\text{phenol}} = \frac{1.05}{12}$$

This last solution is recycled via the reagents tank C2 into the process.

The aqueous phase leaving the extraction column S is final sodium orthohydroxymandelate solution which, after elimination of the remainder of the solvent by steam, will be able to serve as raw material.

Samples were taken from reactors R1, R2 and R3, from solvent 1 and aqueous 1 phases of MD1, from solvent 2 and aqueous 2 phases of MD2, and the final sodium orthohydroxymandelate solution, and analysed by high-pressure liquid chromatography (HPLC).

The selectivity of the reaction was also determined, calculated according to equation 1:

$$S = \frac{100 \times \text{mole OHMNa}}{\text{mole OHMNa} + \text{mole PHMNa} = 2 \text{ moles Na diglycolate}}$$

and the yield of the reaction according to equation 2:

$$R = \frac{(\text{mole OHMNa} + \text{mole PHMNa} = 2 \text{ moles Na diglycolate})}{\text{mole free or salified glyoxylic acid}} \times 100$$

The results recorded in the following table are expressed in molar percentages:

| | OHMNA | PHMNa | Diglycolates | Selectivity | Yield |
|---|---|---|---|---|---|
| Reactor R1 | 0.25 | 0.025 | — | 90.9 | 27.5 |
| Reactor R2 | 0.69 | 0.11 | 0.005 | 85.2 | 81 |
| Reactor R3 | 0.81 | 0.13 | 0.01 | 84.4 | 96 |
| Solvent phase 1 | 0.04 | 0.01 | — | | |
| Aqueous phase 1 | 0.77 | 0.13 | 0.01 | | |
| Solvent phase 2 | 0.05 | — | — | | |
| Aqueous phase 2 | 0.035 | — | — | | |
| Aqueous solution OHMNa | 0.77 | 0.13 | 0.01 | 83.7 | 92 |

It will be seen that the selectivity and yield of the continuous synthesis are comparable in all respects with those described in FR-A-2,687,143.

I claim:

1. Industrial process for the continuous manufacture of sodium orthohydroxymandelate by condensation of phenol in an inert atmosphere with glyoxylic acid in aqueous solution, in the presence of a tertiary amine and of catalytic quantities of a trivalent metal cation at a temperature below 100° C., characterized by the fact that the process is carried out continuously in at least two reactors (R1 . . . Rn) installed in series, the first being supplied by a first tank C1 containing the glyoxylic acid and the trivalent metal cations, and by a second tank C2 containing the phenol and the tertiary amine, that the reaction medium obtained at the outlet of the last of the at least two reactors and consisting of an aqueous phase and an organic phase is transferred into the first of two mixer-decanters (MD1 and MD2) installed in series, that the aqueous phase of the first mixer-decanter MD1 is recovered in order to extract the expected sodium orthohydroxymandelate from it, while the organic phase that has come from MD1 is transferred into the second mixer-decanter MD2 and washed with water, and that the organic phase of the second mixer-decanter MD2 is transferred to the second tank (C2).

2. Process according to claim 1, characterized by the fact that the organic phase that has come from the second mixer-decanter MD2 is mixed with an aqueous solution of phenol and concentrated in order to eliminate all or part of the aqueous phase, then sent to the second tank (C2).

3. Process according to claim 2, characterized by the fact that the aqueous phase coming from the first mixer-decanter (MD1) is sent into an extraction column (S) where it is mixed with a ether which dissolves the phenol and the tertiary amine, the organic phase resulting from this being sent to the second tank (C2) at the same time as that which has come from the second mixer-decanter (MD2), while the aqueous phase containing the expected sodium orthohydroxymandelate is recovered.

4. Process according to claim 1, characterized by the fact that the molar proportion of the starting reagents is 1 mole of glyoxylic acid for 1 to 15 moles of phenol, for 0.8 to 1.2 moles of tertiary amine, and for 0.001 to 0.1 mole of trivalent metal cation.

5. Process according to therefor claim 1, characterized by the fact that the tertiary amine is tributylamine, and the trivalent metal cation is aluminium.

6. Process according to therefor claim 5, characterized by the fact that the residence times of the reaction medium in each reactor are such that each is between 30 and 120 minutes.

7. Process according to claim 6, characterized by the fact that the residence time of the reaction medium in each reactor is about 45 minutes.

8. Process according to therefor claim 7, characterized by the fact that three reactors are used in series (R1, R2, R3), and by the fact that the first reactor (R1) is kept at a temperature of 30 to 80° C., the second (R2), at a temperature of 70 to 90° C., and the last (R3) at a temperature of 70 to 90° C.

9. Process according to therefor claim 8, characterized by the fact that the process is carried out in three reactors kept at 75±5° C. for the first, 85±5° C. for the second and third reactors.

10. Process according to therefor claim 9, characterized by the fact that an alkaline hydroxide, and an ether which dissolves the phenol and the tertiary amine, are added to the first mixer-decanter MD1.

11. Process according to claim 10, characterized by the fact that the alkaline hydroxide is sodium hydroxide, and the ether is tert-amyl methyl ether (TAME).

12. Process according to claim 3, characterized by the fact that the aqueous phase leaving the extraction column S is the final sought sodium orthohydroxymandelate solution.

13. Process according to claim 1, characterized by the fact that the first reactor is supplied continuously, at a constant rate of feed, with an aqueous solution containing, for 1 mole of glyoxylic acid, 1 to 15 moles of phenol, 0.8 to 1.2 moles of tertiary amine, and 0.001 to 0.1 mole of trivalent metal cation.

14. Process according to claim 1, characterized by the fact that the residence times of the reaction medium in each reactor are such that each is between 30 and 120 minutes.

15. Process according to claim 14, characterized by the fact that the residence time of the reaction medium in each reactor is about 45 minutes.

16. Process according to claim 1, characterized by the fact that three reactors are used in series (R1, R2, R3), and by the fact that the first reactor (R1) is kept at a temperature of 30 to 80° C., the second (R2), at a temperature of 70 to 90° C., and the last (R3) at a temperature of 70 to 90° C.

17. Process according to claim 1, characterized by the fact that the process is carried out in three reactors kept at 75±5° C. for the first, 85±5° C. for the second and third reactors.

18. Process according to claim 1, characterized by the fact that an alkaline hydroxide of sodium or potassium, and an ether which dissolves the phenol and the tertiary amine, are added to the first mixer-decanter MD1.

19. Process according to claim 18, characterized by the fact that the alkaline hydroxide is sodium hydroxide, and the ether is tert-amyl methyl ether (TAME).

20. Process according to claim 4, characterized by the fact that the tertiary amine is tributylamine, and the trivalent metal cation is aluminum.

21. Process according to claim 3, characterized by the fact that the tertiary amine is tributylamine, and the trivalent metal cation is aluminum.

* * * * *